(12) United States Patent
Singh et al.

(10) Patent No.: US 7,446,089 B2
(45) Date of Patent: Nov. 4, 2008

(54) METHODS OF INHIBITING AND TREATING BACTERIAL BIOFILMS BY METAL CHELATORS

(76) Inventors: Pradeep K. Singh, 1136 Kirkwood Ct., Iowa City, IA (US) 52240-5752; Michael J. Welsh, 3460 560th St., Riverside, IA (US) 52322; Everett P. Greenberg, 4020 Stewart Rd. NE., Iowa City, IA (US) 52240

( * ) Notice: Subject to any disclaimer, the term of this patent is extended or adjusted under 35 U.S.C. 154(b) by 2 days.

(21) Appl. No.: 10/958,923

(22) Filed: Oct. 4, 2004

(65) Prior Publication Data

US 2005/0143286 A1 Jun. 30, 2005

Related U.S. Application Data

(63) Continuation of application No. PCT/US03/12128, filed on Apr. 18, 2003.

(60) Provisional application No. 60/373,461, filed on Apr. 18, 2002.

(51) Int. Cl.
*A61K 38/00* (2006.01)
*A61K 39/40* (2006.01)

(52) U.S. Cl. .................. 514/2; 514/6; 514/12; 530/367; 530/400; 435/7.2; 424/9.1

(58) Field of Classification Search ............... 514/2, 514/6, 12; 530/365, 400, 367; 435/7.2, 9.1
See application file for complete search history.

(56) References Cited

U.S. PATENT DOCUMENTS

| 5,198,419 | A |   | 3/1993 | Ando et al. |              |
|-----------|---|---|--------|-------------|--------------|
| 5,688,516 | A | * | 11/1997 | Raad et al. | 424/409 |
| 6,086,921 | A |   | 7/2000 | Domenico |               |
| 6,126,955 | A | * | 10/2000 | Ardehali et al. | 424/422 |
| 6,267,979 | B1 | * | 7/2001 | Raad et al. | 424/405 |
| 6,482,396 | B1 | * | 11/2002 | Braun et al. | 424/50 |
| 2002/0123077 | A1 | | 9/2002 | O'Toole et al. | |

FOREIGN PATENT DOCUMENTS

| EP | 0568200 | 11/1993 |
| WO | WO-98/06425 A1 | 2/1998 |

OTHER PUBLICATIONS

Darby, Creg, et al., "Innate defense evicts bacterial squatters," *Nature Immunology*, vol. 3(7):602-604 (2002).
Peterson, M.G., et al., "A Second Antigenic Heat Shock Protein of Plasmodium falciparum," *DNA*, vol. 7(2):71-78 (1988).
Jackson, F. Rob, et al., "Drosophila GABAergic Systems: Sequence and Expression of Glutamic Acid Decarboxylase," *Journal of Neurochemistry*, vol. 54(3):1068-1078 (1990).
International Search Report for International Application No. PCT/US03/12128.

* cited by examiner

*Primary Examiner*—Chih-Min Kam
(74) *Attorney, Agent, or Firm*—Lahive & Cockfield, LLP; Maria Laccotripe Zacharakis; Deborah L. Nagle

(57) ABSTRACT

The invention presented herein provides methods and compositions for the prevention and treatment of bacterial infections. The methods are based on the discovery that depletion of bioavailable iron stimulates surface motility in bacteria thus inhibiting the ability of a bacterial population to develop into a biofilm.

21 Claims, 9 Drawing Sheets

-Lactoferrin

-Lactoferrin

-Lactoferrin

-Lactoferrin

+Lactoferrin

+Lactoferrin

+Lactoferrin

+Lactoferrin

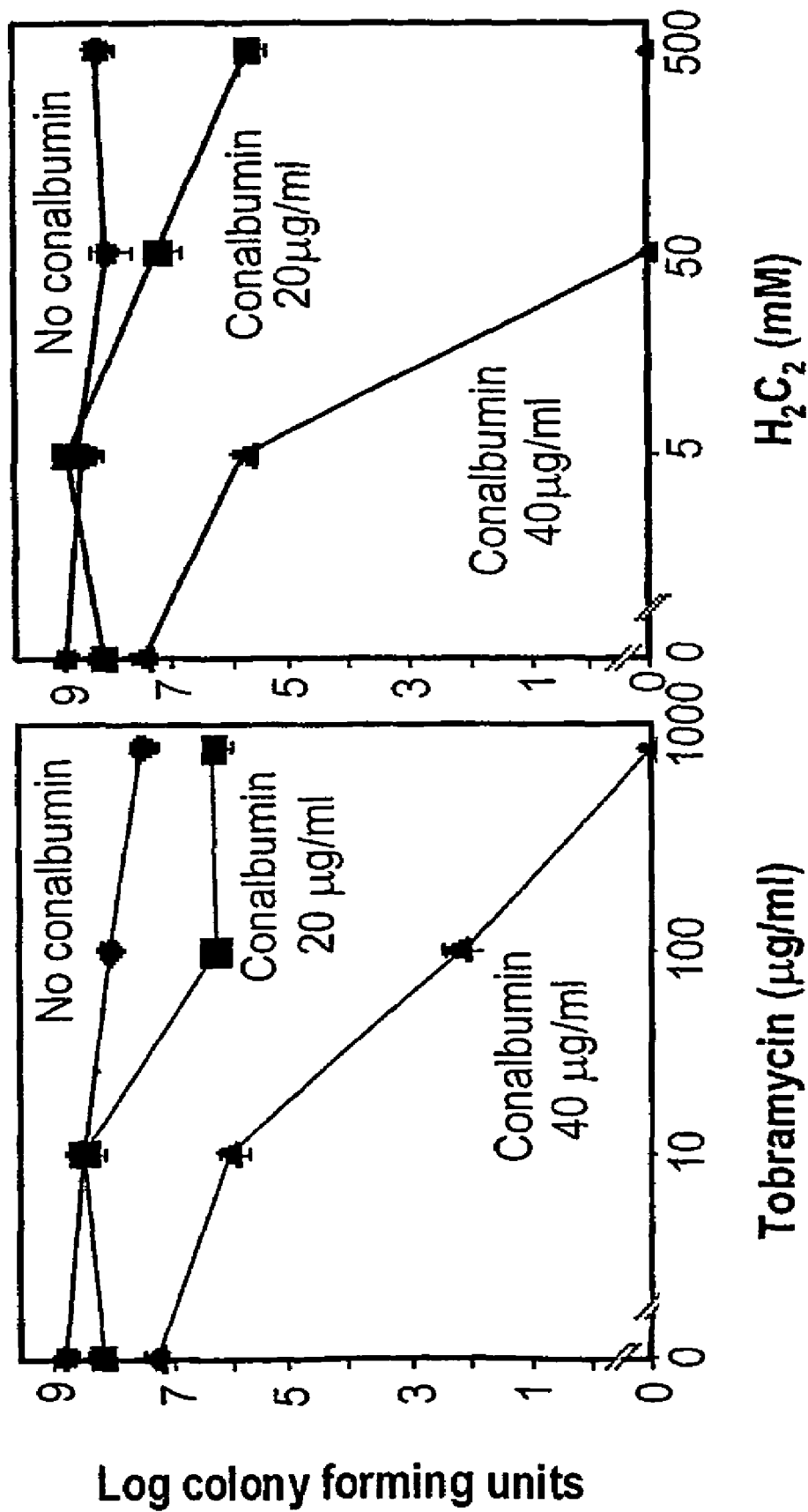

METHODS OF INHIBITING AND TREATING BACTERIAL BIOFILMS BY METAL CHELATORS

RELATED APPLICATIONS

This application claims the priority to PCT/US03/12128, filed on Apr. 18, 2003, which claims the benefit of provisional application Ser. No. 60/373,461, filed Apr. 18, 2002, the entire contents of which are incorporated herein by this reference.

BACKGROUND

Antimicrobial factors form one arm of the innate immune system which protects mucosal surfaces from bacterial infection. These factors can rapidly kill bacteria deposited on mucosal surfaces and prevent acute invasive infections. In many chronic infections, however, bacteria live in biofilms; i.e., distinct, matrix-encased communities specialized for surface persistence. The transition from a free-living, independent existence to a biofilm lifestyle can be devastating because biofilms notoriously resist killing by host defense mechanisms and antibiotics.

Biofilms are defined as an association of microorganisms, e.g., single or multiple species, that grow attached to a surface and produce a slime layer that provides a protective environment (Costerton, J. W. (1995) *J Ind. Microbiol.* 15(3):137-40, Costerton, J. W. et al. (1995) *Annu Rev Microbiol.* 49:711-45). Typically, biofilms produce large amounts of extracellular polysaccharides, responsible for the slimy appearance, and are characterized by an increased resistance to antibiotics (1000- to 1500-fold less susceptible). Several mechanisms are proposed to explain this biofilm resistance to antimicrobial agents (Costerton, J. W. et al. (1999) *Science.* 284(5418): 1318-22).

One theory is that the extracellular matrix in which the bacterial cells are embedded provides a barrier toward penetration by the biocides. A further possibility is that a majority of the cells in a biofilm are in a slow-growing, nutrient-starved state, and therefore not as susceptible to the effects of anti-microbial agents. A third mechanism of resistance could be that the cells in a biofilm adopt a distinct and protected biofilm phenotype, e.g., by elevated expression of drug-efflux pumps.

In most natural settings, bacteria grow predominantly in biofilms. Biofilms of *P. aeruginosa* have been isolated from medical implants, such as indwelling urethral, venous or peritoneal catheters (Stickler, D. J. et al. (1998) *Appl Environ Microbiol.* 64(9):3486-90). Chronic *P. aeruginosa* infections in cystic fibrosis lungs are considered to be biofilms (Costerton, J. W. et al. (1999) *Science.* 284 (5418):1318-22). *P. aeruginosa* is also of great industrial concern (Bitton, G. (1994) Wastewater Microbiology. Wiley-Liss, New York, N.Y.; Steelhammer, J. C. et al. (1995) *Indust. Water Treatm.* :49-55). The organism grows in an aggregated state, the biofilm, which causes problems in many water-processing plants. Of particular public health concern are food processing and water purification plants. Problems include corroded pipes, loss of efficiency in heat exchangers and cooling towers, plugged water injection jets leading to increased hydraulic pressure, and biological contamination of drinking water distribution systems (Bitton, G. (1994) Wastewater Microbiology. Wiley-Liss, New York, N.Y., 9). The elimination of biofilms in industrial equipment has so far been the province of biocides. Biocides, in contrast to antibiotics, are antimicrobials that do not possess high specificity for bacteria, so they are often toxic to humans as well. Biocide sales in the US run at about $1 billion per year (Peaff, G. (1994) *Chem. Eng. News:* 15-23).

A particularly ironic connection between industrial water contamination and public health issues is an outbreak of *P. aeruginosa* peritonitis that was traced back to contaminated poloxamer-iodine solution, a disinfectant used to treat the peritoneal catheters. *P. aeruginosa* is commonly found to contaminate distribution pipes and water filters used in plants that manufacture iodine solutions. Once the organism has matured into a biofilm, it becomes protected against the biocidal activity of the iodophor solution. Hence, a common soil organism that is harmless to the healthy population, but causes mechanical problems in industrial settings, ultimately contaminated antibacterial solutions that were used to treat the very people most susceptible to infection.

*P. aeruginosa* is a soil and water bacterium that can infect animal hosts. Normally, the host defense system is adequate to prevent infection. However, in immunocompromised individuals (such as burn patients, patients with cystic fibrosis, or patients undergoing immunosuppressive therapy), *P. aeruginosa* is an opportunistic pathogen, and infection with *P. aeruginosa* can be fatal (Govan, J. R. et al. (1996) *Microbiol Rev.* 60(3):539-74; Van Delden, C. et al. (1998) *Emerg Infect Dis.* 4(4): 551-60).

For example, Cystic fibrosis (CF), the most common inherited lethal disorder in Caucasian populations (~1 out of 2,500 life births), is characterized by bacterial colonization and chronic infections of the lungs. The most prominent bacterium in these infections is *P. aeruginosa*. By their mid-twenties, over 80% of people with CF have *P. aeruginosa* in their lungs (Govan, J. R. et al. (1996) *Microbiol Rev.* 60(3):539-74). Although these infections can be controlled for many years by antibiotics, ultimately the *P. aeruginosa* bacteria form a biofilm that is resistant to antibiotic treatment. At this point the prognosis is poor. The median survival age for people with CF is the late 20s, with *P. aeruginosa* being the leading cause of death (Govan, J. R. et al. (1996) *Microbiol Rev.* 60(3):539-74). According to the Cystic Fibrosis Foundation, treatment of CF cost more than $900 million in 1995.

In addition, about two million Americans suffer serious burns each year, and 10,000-12,000 die from their injuries. The leading cause of death is infection (Lee, J. J. et al. (1990) *J Burn Care Rehabil.* 11(6):575-80). *P. aeruginosa* bacteremia occurs in 10% of seriously burned patients, with a mortality rate of 80% (Mayhall, C. G. (1993) p. 614-664, Prevention and control of nosocomial infections. Williams & Wilkins, Baltimore; McManus, A. T et al. (1985) *Eur J Clin Microbiol.* 4(2):219-23).

Such infections are often acquired in hospitals ("nosocomial infections") when susceptible patients come into contact with other patients, hospital staff, or equipment. In 1995 there were approximately 2 million incidents of nosocomial infections in the U.S., resulting in 88,000 deaths and an estimated cost of $4.5 billion (Weinstein, R. A. (1998) *Emerg Infect Dis.* 4(3):416-20). Of the AIDS patients mentioned above who died of *P. aeruginosa* bacteremia, more than half acquired these infections in hospitals (Meynard, J. L. et al. (1999) *J Infect.* 38(3):176-81).

Nosocomial infections are especially common in patients of intensive care units as these people often have weakened immune systems and are frequently on ventilators and/or catheters. Catheter-associated urinary tract infections are the most common nosocomial infection (Richards, M. J. et al. (1999) *Crit Care Med.* 27(5):887-92) (31% of the total), and *P. aeruginosa* is highly associated with biofilm growth and catheter obstruction. While the catheter is in place, these infections are difficult to eliminate (Stickler, D. J. et al. (1998) *Appl Environ Microbiol.* 64(9):3486-90). The second most frequent nosocomial infection is pneumonia, with *P. aeruginosa* the cause of infection in 21% of the reported cases (Richards, M. J. et al. (1999) *Crit Care Med.* 27(5):887-92). The annual costs for diagnosing and treating nosocomial pneumonia has been estimated at greater than $2 billion (Craven, D. E. et al. (1991) *Am J Med.* 91(3B):44S-53S).

Treatment of these so-called nosocomial infections is complicated by the fact that bacteria encountered in hospital settings are often resistant to many antibiotics. In June 1998, the National Nosocomial Infections Surveillance (NNIS) System reported increases in resistance of *P. aeruginosa* isolates from intensive care units of 89% for quinolone resistance and 32% for imipenem resistance compared to the years 1993-1997 (NNIS. www.cdc.gov/ncidod/hip/ NNIS/AR_Surv 1198.htm). In fact, some strains of *P. aeruginosa* are resistant to over 100 antibiotics (Levy, S. (March 1998) *Scientific American.*). There is a critical need to overcome the emergence of bacterial strains that are resistant to conventional antibiotics (Travis, J. (1994) *Science.* 264:360-362).

Methods of inhibiting biofilm formation in medical and industrial settings have previously been developed using metal chelators. These methods have disclosed the use of small molecule chelators, i.e., EDTA, EGTA, deferoxamine, detheylenetriamine penta acetic acid and etidronate for the inhibition of biofilm. For example, U.S. Pat. No. 6,267,979 discloses the use of metal chelators in combination with antifungal or antibiotic compositions for the prevention of biofouling in water treatment, pulp and paper manufacturing, and oil field water flooding; U.S. Pat. No. 6,086,921 discloses the use of thiol containing compounds in combination with heavy metals as biocides; and U.S. Pat. No. 5,688,516 discloses the use of non-glycopeptide antimicrobial agents in combination with divalent metal chelating agents for use in the treatment and preparation of medical indwelling devices.

There still exists a need in the medical, environmental and industrial community for the control of biofilm formation. The control of biofilms needs to begin at the level of biofilm formation because, once formed, biofilms are exquisitely resistant to all common bactericidal methods. The present invention provides methods and compositions for inhibiting biofilm formation by chelating metal ions and provides methodology for the treatment of subjects with a bacterial infection prior to biofilm development.

SUMMARY OF THE INVENTION

In general, the invention provides a method to inhibit bacterial biofilm formation. The inhibition of biofilms allows for removal of potentially harmful bacteria. More particularly, the invention is based on the discovery that by limiting the amount of iron that is available to a population of bacteria, biofilm formation can be inhibited.

In one aspect, the invention provides a method of inhibiting biofilm formation by bacteria by contacting the bacteria with a metal chelator.

In another aspect, the invention provides a method of inhibiting biofilm formation by contacting a bacterial population with a metal chelator such that the lack of metal ions stimulates surface motility.

The invention also provides a method of inhibiting biofilm development in a subject by administering a metal chelator. Administration of a metal chelator will inhibit biofilm formation and allow the subject's immune system and/or antibiotics or other antibacterial agents to kill the bacteria.

Another aspect of the invention provides a method of treating a subject suffering from a bacterial infection by administering to the subject a composition containing a metal chelator. The composition may also include an antibacterial agent such as an antibiotic.

In another aspect, the invention provides a method of inhibiting biofilm formation on a medical indwelling device in a subject by administering to the subject a metal chelator. These devices, for example, may include catheters, pacemakers, or orthopedic devices.

In another aspect, the invention provides a microbial disinfectant containing a metal chelator. The disinfectant can also contain a biocide or an antibiotic.

In another aspect, the invention provides a pharmaceutical composition containing a therapeutically effective amount of a metal chelator and a pharmaceutically acceptable carrier. This composition can also contain an antibacterial agent such as an antibiotic.

In another aspect, the invention provides a method of inhibiting biofilm on a piece of equipment, e.g., a device, by contacting, e.g., bathing or coating, the equipment with a metal chelator such that any bacteria on the equipment are not able to form a biofilm. This application is particularly useful in industrial settings such as, for example, medical, water treatment, pulp and paper manufacturing and oil field water flooding.

The methods of the current invention are particularly effective when the metal chelator is applied prior to the point at which the bacteria stop roaming as, individuals. Therefore, in one aspect the invention provides methods of inhibiting biofilm development by contacting a bacterial population with a metal chelator prior to the point when the bacteria stop roaming as individuals In another aspect, the invention provides a kit containing a metal chelator and instructions for use. In a related aspect, the kit may contain an antibacterial agent such as an antibiotic.

In another aspect, the methods of the invention further comprise the step of obtaining the metal chelator.

In accordance with one embodiment of the invention, the metal chelator is a non-proteinaceous metal chelator. In accordance with another embodiment of the invention, the metal chelator is a proteinaceous metal chelator.

For example, a proteinaceous metal chelator in accordance with the invention can be a naturally occurring polypeptide, or fragment of a naturally occurring polypeptide, that has the ability to sequester metal ions; or, conversely, can be an engineered polypeptide. In particular embodiments, the metal chelator can be specific for iron. For example, the proteinaceous metal chelator can be a known iron chelating protein such as lactoferrin or conalbumin.

The metal chelators of the invention are useful against pathogenic bacteria. For example, in certain embodiments, proteinaceous metal chelators are useful against *Pseudomonas aeruginosa*.

BRIEF DESCRIPTION OF THE DRAWINGS

FIGS. 5A-B depict the effect of conalbumin on the antimicrobial susceptibility of *P. aeruginosa* biofilms to tobramycin.

DETAILED DESCRIPTION OF THE INVENTION

Definitions

Figure 1:
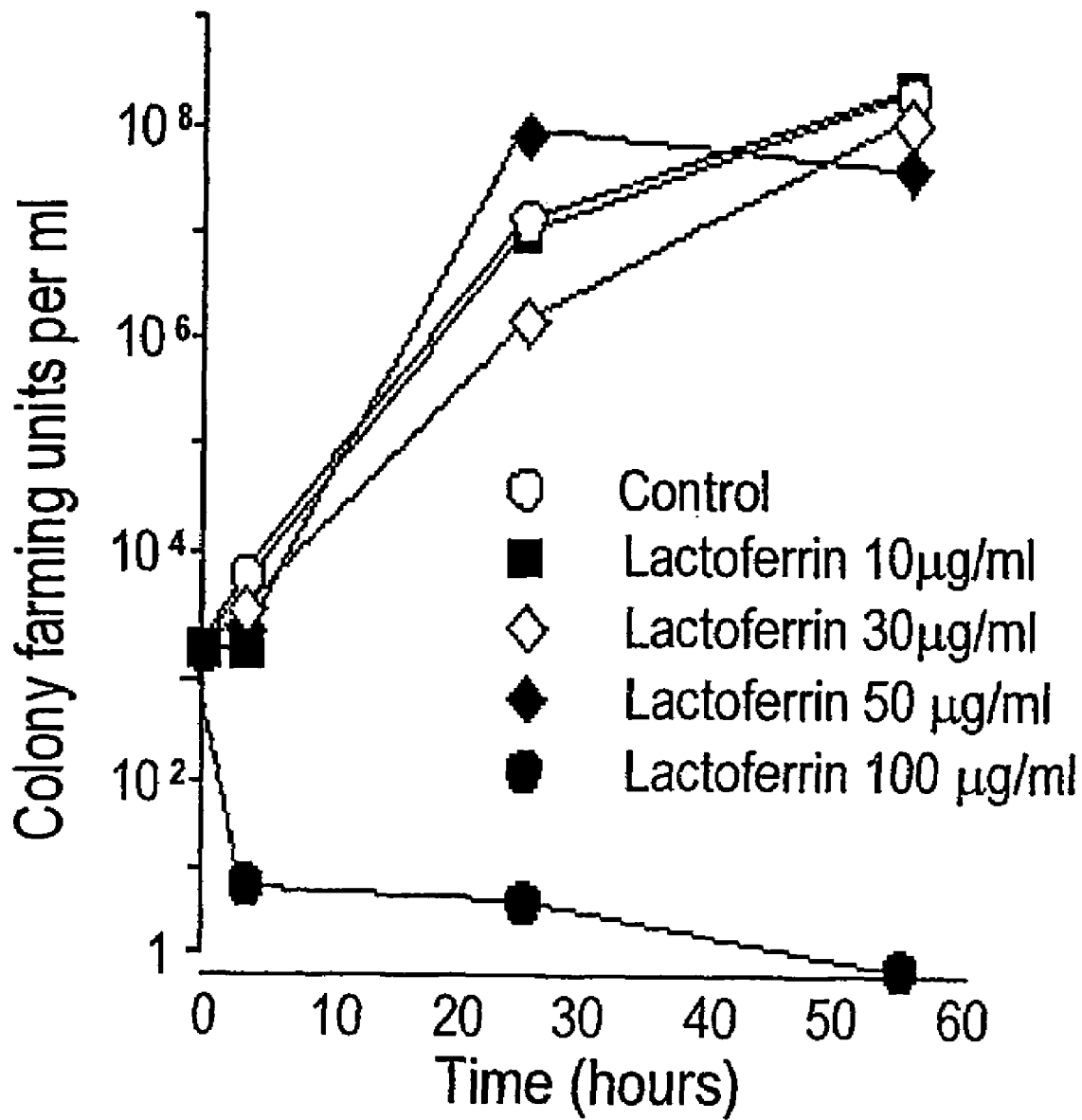
FIG. 1 depicts the growth of *P. aeruginosa* in the presence of lactoferrin.

Before further description of the invention, certain terms employed in the specification, examples and appended claims are, for convenience, collected here.

The term "amino acid" as used herein, refers to naturally and non-naturally occurring amino acids, and residues thereof. Thus, the term is intended to include analogs, derivatives and congeners of any specific amino acids, and residues thereof.

The term "antibacterial agent" refers to any substance that is either bactericidal or bacteriostatic, i.e., capable of killing or inhibiting the growth of bacterial cells.

The term "antibiotic" refers to a chemical substance produced by a microorganism, which has the capacity to inhibit the growth of or to kill other microorganisms. The "term" antibiotic also refers to synthetically made compounds that have the capacity to inhibit the growth of or to kill a microorganism (e.g., a bacterium).

The term "biocide" refers to a substance that is that is capable of killing a living organism, or that is any substance that is toxic to living organisms.

The term "biofilm" refers to a population of a bacteria growing on a surface, wherein the bacteria are encased in a matrix of polysaccharides, glycoproteins or nucleic acids. In this state, bacteria are highly resistant to both phagocytes and antibiotics. The term "biofilm" is further intended to include biological films that develop and persist at interfaces in aqueous environments. Biofilms are composed of microorganisms embedded in an organic gelatinous structure composed of one or more matrix polymers which are secreted by the resident microorganisms.

The language "biofilm development" or "biofilm formation" is intended to include the formation, growth, and modification of the bacterial colonies-contained with biofilm structures, as well as the synthesis and maintenance of the exopolysaccharide matrix of the biofilm structures.

The term "engineered polypeptide" refers to any polypeptide that has at least one altered amino acid such that it performs a desired function. The altered amino acid or acids may be natural amino acids or artificial amino acids (e.g., analogs or mimetics). Thus, the "engineered polypeptides" are intended to include compounds composed, in whole or in part, of peptidomimetic structures, such as D-amino acids, non-naturally occurring L-amino acids, modified peptide backbones, and the like. Engineered peptides can be produced synthetically or recombinantly. Methods for preparing peptidomimetics are known in the art. For example, a peptidomimetic can be derived as a retro-inverso analog of the peptide. Such retro-inverso analogs can be prepared according to methods know in the art (see, e.g., U.S. Pat. No. 4,522,752.)

The terms "effective amount" and "therapeutically effect amount" are used interchangeably and are intended to include the amount of a compound of the invention given or applied to an organism or subject that allows the compound to perform its intended therapeutic function. The effective amounts of the compound of the invention will vary according to factors such as the degree of infection in the subject, the age, sex, and weight of the subject. Dosage regimes can be adjusted to provide the optimum therapeutic response. For example, several divided doses can be administered daily or the dose can be proportionally reduced as indicated by the exigencies of the therapeutic situation.

The term "flyer" refers to a behavior of bacterial cells that have detached from the surface where they were grown and are swept away by the flow of medium.

The term "fragment" refers to any portion of a naturally occurring polypeptide. A fragment can be made synthetically, enzymatically, or recombinantly. In one embodiment of the invention, a fragment is a portion of a naturally occurring polypeptide that retains the ability to chelate iron.

The term "medical indwelling device" refers to any medical device implanted or inserted in the human body. Such devices can be temporarily or permanently implanted or inserted. A medical indwelling device can be, for example, catheters, orthopedic devices, prosthetic devices, vascular stents, urinary stents, pacemakers, or implants.

The term "metal chelator" is intended to describe any substance that is able to remove a metal ion from a solution system by forming a new complex ion, that has different chemical properties than those of the original metal ion. The term is further intended to encompass substances that are capable of chelating metal ions, specifically divalent metals. Metal chelators in accordance with the invention can be non-proteinaceous metal chelators or proteinaceous metal chelators.

The term "metal ions" is intended to include any metal ion that is bioavailable, i.e., any metal ion involved in a biochemical reaction or pathway, or any metal ions that is available in the fluid, tissue or bone of a subject.

The term "non-proteinaceous metal chelator" refers to a metal chelator that does not comprise protein or protein-like moieties. In other words, a non-proteinaceous metal chelator is not peptide based and does not contain amino acids. Advantageously, non-proteinaceous metal chelators are small molecules; i.e., organic non-peptidic compounds.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% of active ingredient in combination with a pharmaceutically acceptable carrier. Pharmaceutical compositions of the current invention may further contain a biocide, antimicrobial, or antibiotic.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "proteinaceous" as used herein refers to molecules comprising protein or protein-like moieties. Thus, the term encompasses molecules that are naturally occurring proteins, fragments of naturally occurring proteins, and engineered polypeptides comprising naturally occurring amino acids, analogs of naturally occurring amino acids, and combinations thereof.

The terms "protein" and "polypeptide" are used interchangeably herein. The term "peptide" is used herein to refer to a chain of two or more amino acids or amino acid analogs (including non-naturally occurring amino acids), with adjacent amino acids joined by peptide (—NHCO—) bonds. Thus, peptides in accordance with the invention include oligopeptides, polypeptides, proteins, and peptidomimetics.

The term "rambler" refers to bacterial cells that move away from the site of cell division in response to an external stimulus.

The term "squatter" refers to bacterial cells that remain stationary on a surface from the time they are created by cell division to the time they themselves divided.

The term "surface motility" refers to the capacity of bacteria to translocate over surfaces. Surface motility can be divided into two distinct behaviors. The first, termed "twitching", is a type of translocation used by bacteria to move over surfaces using pili. The second, termed "swarming", is a social motility in which groups of bacteria move together over a surface. The mechanism of swarming is not completely characterized as of yet.

The term "subject" includes organisms which are can suffer from biofilm-associated states. The term subject includes mammals, e.g., horses, monkeys, bears, dogs, cats, mice, rabbits, cattle, squirrels, rats, and, preferably, humans. In a further embodiment, the subject may be immunocompromised.

Overview of the Invention

Biofilms are known to be problematic in many settings including medical, industrial and mechanical environments. The inventors disclose herein a novel method to inhibit biofilm formation. It has been discovered that limiting the amount of bioavailable iron to a population of bacteria drastically inhibits the ability of bacteria to organize into biofilms. By artificially manipulating the amount of iron available, the inventors are able to control the formation, development, persistence and dispersion of microbial biofilms.

In one aspect, the invention provides a method of inhibiting biofilm formation by bacteria by contacting the bacteria with a metal chelator. In one embodiment, the metal chelators of the invention can be proteinaceous. In another embodiment, the chelators can be non-proteinaceous.

Biofilms can be comprised of bacteria, fungi, yeast, protozoa, and other microorganisms. Most commonly biofilms are made of bacteria. Both gram negative and gram positive bacteria are capable of forming biofilms. Examples of gram positive bacteria that are capable of forming biofilms are bacteria from the genus *Staphylococcus* including, but not limited to, organisms from the species *epidermidis* and *aureus*. Examples of gram negative bacteria that are capable of forming biofilms are bacteria from the genuses *Pseudomonas, Klebsiella, Enterobacter, Serratia*, and *Pantoea*. In one embodiment of the invention, the bacteria are *Pseudomonas aeruginosa*.

Many proteins chelate metal ions. Metals such as zinc, lead, iron, copper, calcium, and manganeese are capable of being chelated. Proteins are well known in the art to chelate specific metal ions. For example, the ring finger family of proteins has been shown to chelate zinc; Glucose Regulated Protein 78(GRP78) (Peterson, M. G., et al. (1988) DNA 7, 71-78) has been shown to chelate lead; lactoferrin and conablumin have been shown to chelate iron; metallothionein has been shown to chelate copper; and glutamate decarboxylase C1(Gad C1) (Jackson, F. R., et al. (1990) J. Neurochem. 54 (3), 1068-1078) has been shown to chelate calcium. In one embodiment of the invention, the metal being chelated is iron.

In certain embodiments of the invention, the metal chelator is a proteinaceous iron chelator and, as such, can be a naturally occurring polypeptide, or fragment of a naturally occurring polypeptide that has the ability to sequester metal ions or, conversely, can be an engineered polypeptide with the ability to bind iron. In specific embodiments the proteinaceous metal chelator can be a known iron chelating protein such as, e.g., lactoferrin or conalbumin.

In other embodiments, the metal chelator is a non-proteinaceous iron chelator. In one embodiment of the invention, the non-proteinaceous metal chelators are small molecule metal chelators. In certain embodiments of the invention, the non-proteinaceous iron chelators of the invention exclude those disclosed in the prior art, including those disclosed in U.S. Pat. Nos. 5,688,516, 6,267,979, and U.S. Pat. No. 6,086,921, e.g., EDTA, EGTA, deferoxamine, detheylenetriamine-penta acetic acid and etidronate, for the inhibition of biofilms, e.g., in industrial settings and on medical indwelling devices.

In preferred embodiments of the invention, the non-proteinaceous metal chelators include ethylenediamine-N,N,N',N'-tetraacetic acid (EDTA); the disodium, trisodium, tetrasodium, dipotassium, tripotassiun, dilithium and diammonium salts of EDTA; the barium, calcium, cobalt, copper, dysprosium, europium, iron, indium, lanthanum, magnesium, manganese, nickel, samarium, strontium, and zinc chelates of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid)hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylene diamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11]pentatriacont ane hexahydrobromide; and triethylenetetraminie-N,N,N',N'',N''',N''''-hexaacetic acid.

In another aspect, the invention provides a method of stimulating surface motility in bacteria. Surface motility is exhibited by certain bacterial cells when on surfaces, e.g., solid or semi solid surfaces. Much effort has been invested in recent years to determine the molecular basis of surface motility. Specific genes and pathways that are involved in surface motility have been recently identified, e.g., the Pil genes from *Psuedomonas*.

In one embodiment, the invention provides a method of inhibiting biofilm formation by stimulating surface motility in a bacterial population by contacting the bacteria with a metal chelator, e.g., a proteinaceous or non-proteinaceous metal chelator.

In particular aspects of this embodiment of the invention, the proteinaceous metal chelator can be specific for iron, e.g., lactoferrin or conalbumin. In certain embodiments, the proteinaceous metal chelator can be a naturally occurring polypeptide, or fragment thereof. In other embodiments, the proteinaceous metal chelator can be an engineered polypeptide with the ability to chelate metal. In particular embodiments of the invention, the bacterium in which surface motility is being stimulated is *Psuedomonas aeruginosa*.

In another aspect, the invention provides a method of inhibiting biofihm development in a subject by administering a metal chelator, e.g., a proteinaceous or non-proteinaceous metal chelator. This aspect of the invention is particularly useful in subjects known to have a high risk of developing a bacterial biofilm infection, e.g., cystic fibrosis patients. Studies have shown that the immune system is capable of fighting infections of the bacteria that comprise biofilms as long as they are not assembled into a biofihm. As shown in the Examples below, proteinaceous metal chelators in accordance with the invention inhibit biofilm formation. Thus, administration of a proteinaceous or non-proteinaceous metal chelator would allow the host immune system to effectively combat bacterial infections that would otherwise develop into infections of biofilms.

In certain aspects the biofilm development occurs in the regions of the airway, lungs, eye (e.g., the cornea), ear (e.g., middle ear), mouth (e.g., gums and jawbone), heart, prostate, kidneys or bones. In particular aspects of this embodiment of the invention, the proteinaceous metal chelator can be specific for iron, e.g., lactoferrin or conalbumin. In certain embodiments, the proteinaceous metal chelator can be a naturally occurring polypeptide, or fragment thereof. In other embodiments of the invention, the proteinaceous metal chelator can be an engineered polypeptide with the ability to chelate metal. In particular embodiments of the invention, the bacterium in which surface motility is being stimulated is *Psuedomonas aeruginosa*.

In another aspect, the invention provides a method of treating a subject suffering from a bacterial infection by administering a therapeutically effective amount of a metal chelator, e.g., a proteinaceous or non-proteinaceous metal chelator. In one embodiment, a subject shown to have a bacterial infection by any of a number of other tests, can be administered a metal chelator such that the bacterial infection does not progress to a bacterial biofilm infection. Administration of a metal chelator inhibits the ability of the bacteria to form a biofilm, thus rendering the bacteria susceptible to the immune system of the subject, and/or to antibacterial agents, e.g., antibiotics.

In a related aspect, the metal chelator can be administered in combination with an antibacterial agent. Antibacterial agents include antibiotics, biocides, antimicrobials, and bacteriostatic agents. In one particular embodiment, the proteinaceous metal chelator is administered in combination with an antibiotic. Examples of antibiotics that can be used in combination with a proteinaceous metal chelator include, but are not limited to the following: tobramycin, tazobactam, ciprofloxin, semi-synthetic penicillins, aminoglycosides, fluoroquinones cephlosoprins, and clindamycin.

In one aspect, the invention provides a composition, e.g., a pharmaceutical composition, used to inhibit biofilm formation that includes a therapeutically effective amount of a metal chelator, e.g., a proteinaceous or non-proteinaceous metal chelator, and a pharmaceutically acceptable carrier. The composition can further include an antibiotic. Antibiotics intended for use in this invention include, but are not limited to: broad-spectrum antibiotics (e.g., tetracyclines); medium-spectrum antibiotics (e.g., bacitracin, erythromycins, penicillin, cephalosporins and streptomycins); and narrow spectrum antibiotics (e.g., antibiotics that are effective against only a few species of bacteria, for example, polymixins). In certain particular examples, tobramycin, tazobactam, ciprofloxin, piperacellin semi-synthetic penicillins, amino glycosides, fluoroquinones, cephlosporins, or clindamycin are used in the composition.

In certain embodiments the proteinaceous metal chelator can be a naturally occurring polypeptide, or fragment thereof. In other embodiments of the invention the proteinaceous metal chelator can be an engineered polypeptide with the ability to chelate metal. In particular embodiments of this invention the bacteria is *Psuedomonas aeruginosa*.

Biofilms frequently occur on devices that are implanted in a patient for therapeutic purposes. Such medical indwelling devices include, but are not limited to, contact lenses, catheters, central venous catheters and needleless connectors, endotracheal tubes, orthopedic devices, intrauterine devices, mechanical heart valves, artificial hearts, pacemakers, peritoneal dialysis catheters, prosthetic devices, tympanostomy tubes, urinary catheters, and voice prostheses, vascular stents, urinary stents and implants.

Thus, in another embodiment, the invention provides a method of inhibiting biofilm development on a medical indwelling device. The method comprises administering to an individual with a medical indwelling device an effective amount of a metal chelator, e.g., a proteinaceous or non-proteinaceous metal chelator. In specific embodiments, the medical indwelling devices are catheters, orthopedic devices, prosthetic devices, vascular stents, urinary stents, pacemakers and implants.

In another embodiment, the invention provides a method for inhibiting biofilm formation, and bacterial growth on food. The method comprises contacting the food with an effective amount of a metal chelator, e.g., a proteinaceous or non-proteinaceous metal chelator. The metal chelator may be one component of a composition that further includes an antibacterial agent. In one specific embodiment, the food is a meat.

In another aspect, the invention provides a composition that acts as a microbial disinfectant. In one embodiment, the microbial disinfectant contains an effective amount of a metal chelator, e.g., a proteinaceous or non-proteinaceous metal chelator. In related embodiments, the disinfectant contains a biocide or antibiotic. One example of an application for a microbial disinfectant in accordance with the invention is for use in a hospital or medical setting to disinfect surfaces that sterile instruments come in contact with during routine use.

In another aspect, the invention provides a pharmaceutical composition that contains an effective amount of a metal chelator, e.g., a proteinaceous or non-proteinaceous metal chelator, and a pharmaceutically acceptable carrier. Examples of pharmaceutically acceptable carriers include sugars, cellulose, and its derivatives, talc, excipients, oils, glycols, esters, buffering agents, ethyl alcohol, phosphate buffer solutions; and other non-toxic compatible substances employed in pharmaceutical formulations. In related embodiments, the pharmaceutical composition may contain an antibacterial agent. In a specific embodiment, the antibacterial agent is an antibiotic.

In specific embodiments, the concentration of the proteinaceous metal chelator, e.g., lactoferrin, used in the methods or compositions described herein is between about 5 and about 100 µg/ml. Preferably the concentration of lactoferrin is between about 15 and about 40 µg/ml. More preferably the concentration of lactoferrin is between about 20 and about 30

μg/ml. In a specific embodiment of the invention, the concentration of lactoferrin is about 20 μg/ml.

In another aspect of the invention, the metal chelator, e.g., a proteinaceous or non-proteinaceous metal chelator, is part of a kit that includes instructions for use. The kit may be used for the treatment of a subject with a bacterial infection, for prevention of biofilm development on a medically implanted device, or to inhibit biofilm development in an industrial or medical setting. The kit may contain an antimicrobial agent, e.g., an antibiotic.

The methods of the invention disclosed herein may further comprise the step of obtaining the metal chelator, e.g., a proteinaceous or non-proteinaceous metal chelator.

Exemplification

The invention is further illustrated by the following examples which should not be construed as limiting.

Materials and Methods

The following methods apply to the Examples described below.

Bacterial Strains, Plasmids, and Growth Conditions

*P. aeruginosa* strain PAO1 containing the GFP plasmid pMRP9-1 was used for most studies. Where indicated, an isogenic surface motility mutant (a PAO1 pilHIJK deletion mutant from J. Kato (Department of Fermentation Technology, Hiroshima University, Hiroshima, Japan.) containing pMRP9-1 was used. Biofilm medium consisted of 1% Trypticase Soy Broth (Difco, Detroit, Mich.). In the growth experiments, approximately $10^3$ bacteria from an overnight culture were added to 5 ml of biofilm medium containing the indicated concentrations of lactoferrin (Sigma Chemical Co., St Louis, Mo.). Cultures were incubated in acid-washed tubes at 37° C. with shaking. Colony-forming units were determined by plate counting. The concentration of lactoferrin that inhibited bacterial growth varied somewhat for different lots of lactoferrin but was never less than 30 μg/ml. *P. aeruginosa* with pMRP9-1 was also grown in lactoferrin-containing effluent medium from flow cells. After one day of bacterial growth, effluent was collected on ice, filter sterilized, and growth was assessed as above.

Bioflim Experiments

For studies of biofilm formation, wild-type *P. aeruginosa* PAO1 and the surface motility mutant were grown in flow cells similar to those described previously; the size of the flow channel was 5×35×1 mm. An overnight culture diluted to $10^7$ cells per ml in fresh biofilm medium was used as the inoculum and flow was arrested for 45 min. Flow of biofilm medium with and without 20 μg/ml of Fe-unsaturated or Fe-saturated lactoferrin or conalbumin (Sigma Chemical Co.) was then initiated at a rate of 170 μl/min. Images were obtained using a Biorad (Hercules, Calif.) scanning confocal microscope.

Bacterial movement was assessed by using time-lapse images acquired at 1 min intervals. Motion of bacterial cells was traced visually by following individual cells. VOXblast software (VayTek, Inc, Fairfield, Iowa) was used to obtain the X-Y coordinates of bacterial cells.

Bacterial behaviors were classified as follows. Squatters remained within a 15 μm circle drawn around the point of parental cell division until the time of its cell division. Ramblers remained attached to the growth surface, but moved outside the circle. Flyers detached and were carried away by media flow. Dividing times of attached bacteria were measured by counting the number of frames between cell divisions; 60 bacterial divisions were observed and the dividing times were averaged.

*P. aeruginosa* biofilms for susceptibility tests were grown in a rotating disk reactor. Fe-unsaturated conalbumin (Sigma Chemical Co.) was added to standard biofilm medium at indicated concentrations for the duration of biofilm growth. Discs and attached bacteria were then washed 3 times in distilled water, and treated for 4 h in 1 ml of $H_2O_2$ (Fisher Scientific) or tobramycin (Eli Lilly, Indianapolis, Ind.) at indicated concentrations. The treated discs were washed 3 times, and bacteria were removed and dispersed in 2 ml sterile PBS by homogenization (Brinkman Homogenizer, model 10/35). Viable cell numbers were enumerated by plate counting.

Surface Motility Assays

Plates for surface motility assays consisted of biofilm medium plus 1% Noble agar (Difco, Detroit, Mich.). Indicated concentrations of deferoxamine and $FeCl_3$ (Sigma Chemical Co.) were added to molten agar. Plates were dried overnight at room temperature, and *P. aeruginosa* with pMRP9-1 was point inoculated at the bottom of the Petri plate. After 3 days, the surface distance along the plastic-agar interface (at the bottom of the agar plate) was measured.

EXAMPLE 1

Effect of Lactoferrin on Bioflim Formation

At high concentrations, lactoferrin is known to limit bacterial growth by sequestering iron. In this regard, lactoferrin acts like other nutrient-depriving host defense molecules, such as transcobalamins (which bind vitamin B12), and calprotectin (which binds zinc). Lactoferrin can also be bactericidal by binding lipopolysaccharide and disrupting bacterial membranes, and it can enhance killing by other antibiotics.

To determine whether lactoferrin has anti-biofilm activity that is distinct from these known properties, the effect of a sub-inhibitory concentration of lactoferrin (20 μg/ml) on biofilm development was examined. This concentration of lactoferrin did not affect the growth rate of free swimming *P. aeruginosa* PAO1 (FIG. 1).

Figure 2A:
FIGS. 2A-H depict confocal microscopic images of GFP-labeled *P. aeruginosa* in biofilm flow cells.
Figure 2B:
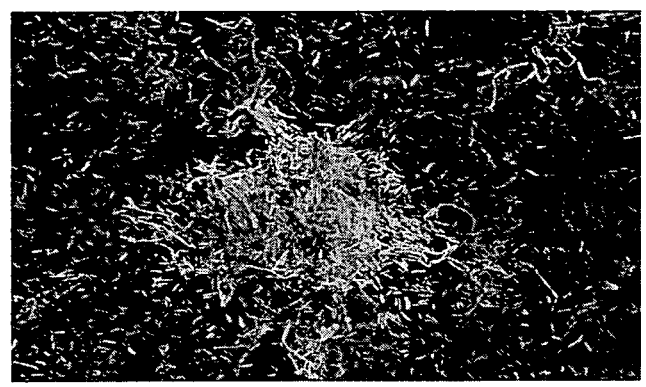
Figure 2C:
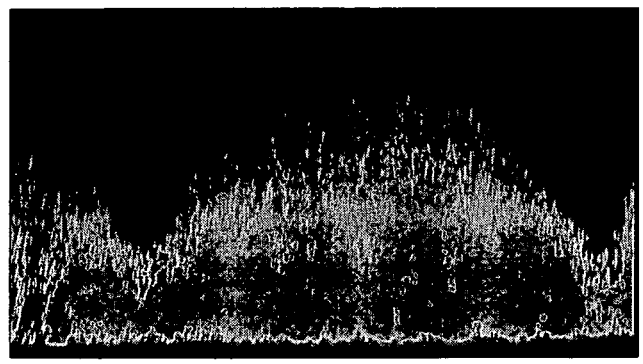
Figure 2D:
Figure 2E:
Figure 2F:
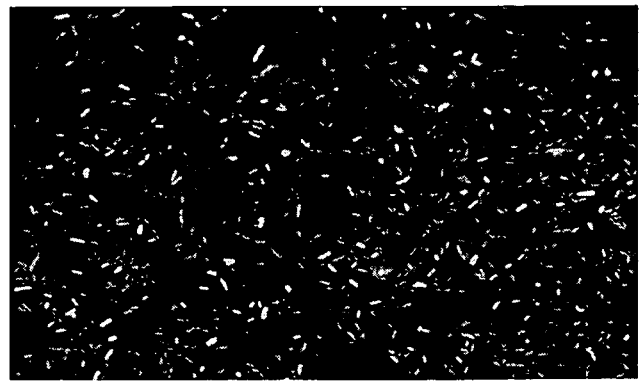
Figure 2G:
Figure 2H:

To evaluate the effect of lactoferrin on biofilm formation, *P. aeruginosa* expressing green fluorescent protein (GFP) was grown in continuous culture flow cells and followed biofilm development over time. Flow cell chambers were continuously perfused with biofilm medium with or without lactoferrin. In medium without lactoferrin (FIGS. 2a-d), the typical stages of biofilm development were observed. Initially, bacteria attached to the surface (FIG. 2a). Microcolonies were evident after 24 h (FIG. 2b). After 3 days, the microcolonies had enlarged (FIG. 2c). By day 7, towering pillar and mushroom shaped biofilms had developed (FIG. 2d). Lactoferrin disrupted this pattern of development (FIGS. 2e-h). Attached bacteria (FIG. 2e) multiplied, but they failed to form microcolonies (FIG. 2f). Even after a prolonged incubation, the bacteria did not assemble into differentiated biofilm structures; in the presence of lactoferrin they remained in a thin layer (FIGS. 2g and h). In contrast, exposing mature, 5 day-old biofilms to lactoferrin-containing medium for 48 h failed to alter their structure. Thus, once they had developed, biofilms were resistant to lactoferrin. Because lactoferrin prevented biofilm development, additional studies to confirm that the low concentration of lactoferrin did not prevent bacterial growth were performed. To show that lactoferrin-containing medium in flow cells could support growth of *P. aeruginosa* bacteria in the effluent from a biofilm chamber were cultured. *P. aeruginosa* doubled 6 times in 22 h in this conditioned medium, verifying that even spent lactoferrin-treated medium did not limit growth. Second, the dividing times of attached bacteria in flow cells using time-lapse video microscopy were measured. Lactoferrin increased the dividing time of attached cells by 27% (93 min without lactoferrin vs. 127 min with 20 µg/ml lactoferrin). Whereas this reduced growth rate could decrease the size of microcolonies and biofilms, it could not account for the complete absence of biofilm structure induced by lactoferrin.

EXAMPLE 2

Effect of Lactoferrin on Bacterial Motion

Figure 3B:
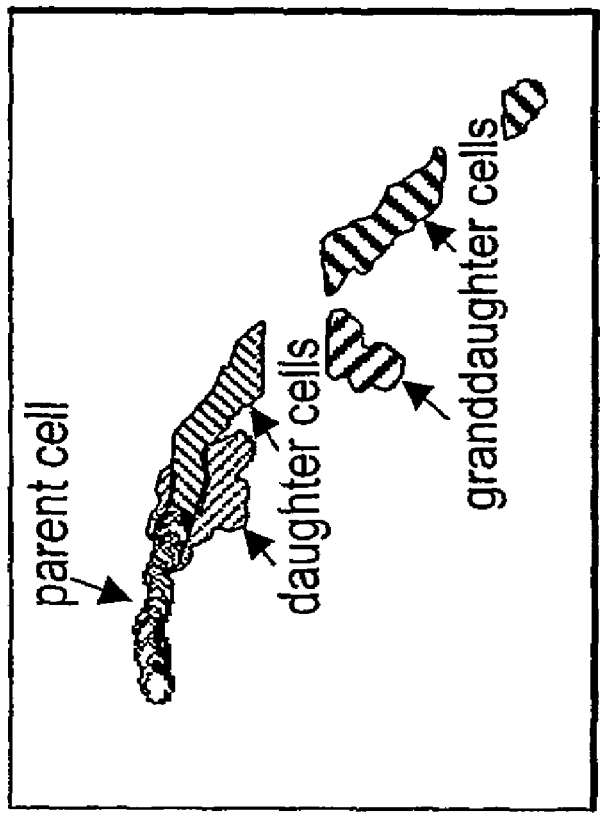
FIGS. 3A-D depict representations of bacterial behaviors without and with lactoferrin.
Figure 3A:
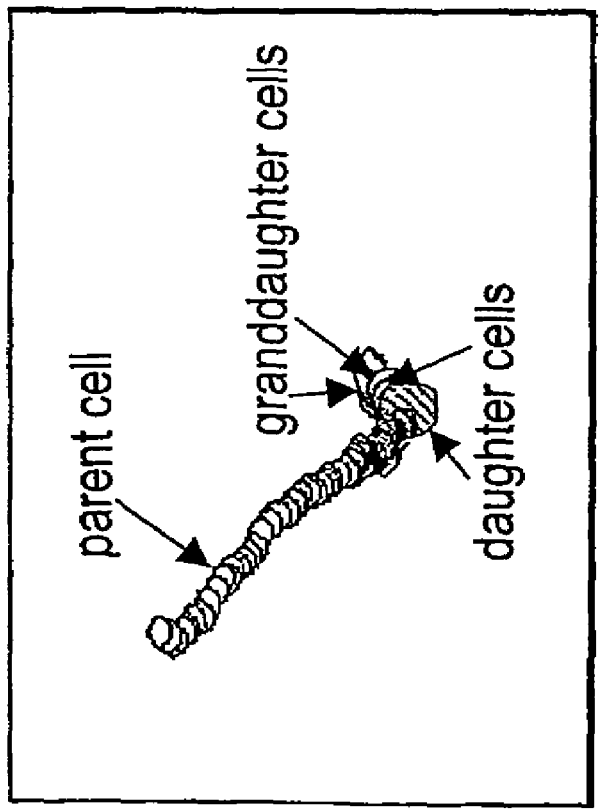
Figure 3D:
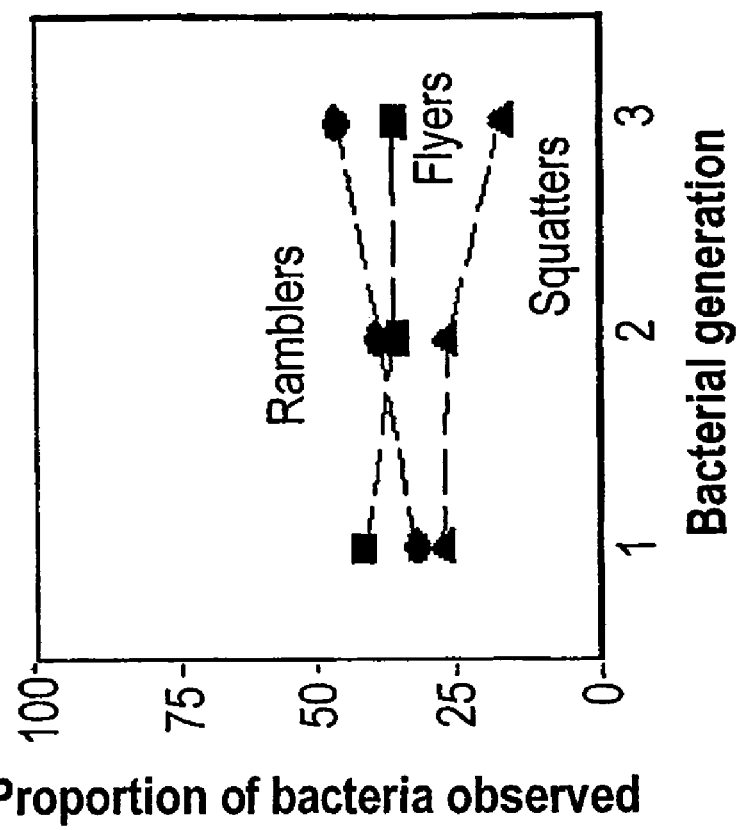

Although the time-lapse microscopy showed only small differences in dividing times, it revealed that lactoferrin strikingly altered bacterial movement. These differences are represented in FIGS. 3a and b, which trace the movement of representative bacteria over the surface of a flow cell. In the absence of lactoferrin (FIG. 3a), the parent bacterium moved across the field of view. When the parent cell divided, the two daughter cells remained near the point of parent cell division. When a daughter cell divided, its progeny also remained near the point of the original cell division. Thus, a microcolony began to form. In the presence of lactoferrin (FIG. 3b), the parental cell also moved across the field of view, and divided into two daughter cells. With lactoferrin, however, the daughter cells moved away from the point of cell division. When one of the daughter cells divided, its progeny also left the site of cell division.

Figure 3C:
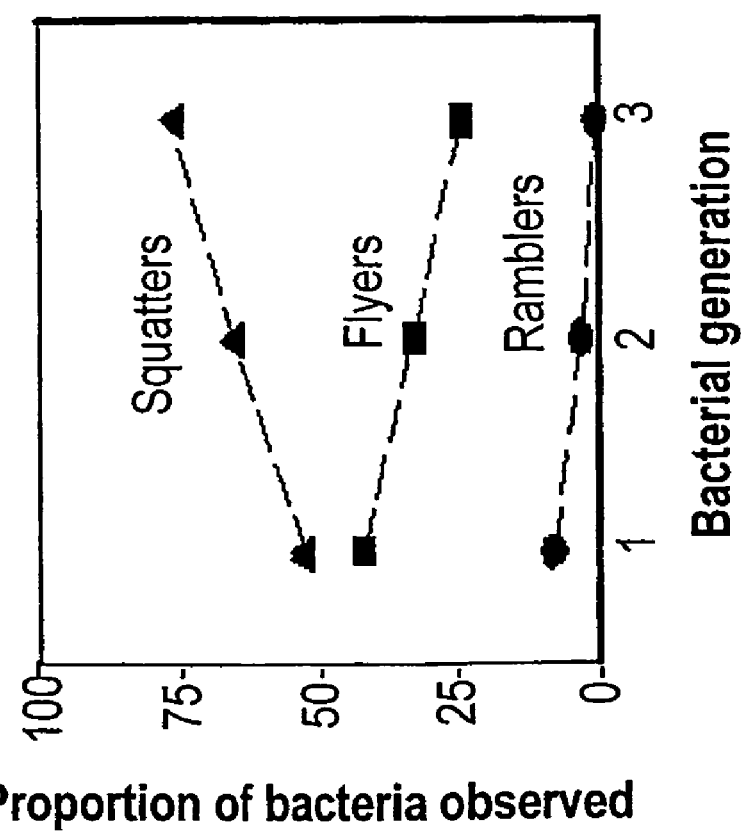

To analyze the changes more quantitatively, three behaviors were defined and the actions of 40 parental cells and their offspring over three generations were classified. Bacteria that remained stationary from the time they were created by cell division to the time they themselves divided were called squatters. Bacteria that moved away from the division site were called ramblers, and cells that detached from the surface and were swept away by the flow of medium were called flyers. FIGS. 3c and d show the relative proportion of bacteria engaged in these different behaviors. In the absence of lactoferrin, the majority of cells were squatters, fewer cells were flyers, and rambling cells were rare. In the presence of lactoferrin, a significantly larger proportion of cells exhibited rambling behavior and fewer were squatters. In both cases, the prevailing behavior (squatting without lactoferrin, and rambling with lactoferrin) became more prevalent in subsequent bacterial generations.

EXAMPLE 3

Effect of Lactoferrin on Biofilm Formation

Figure 4A:
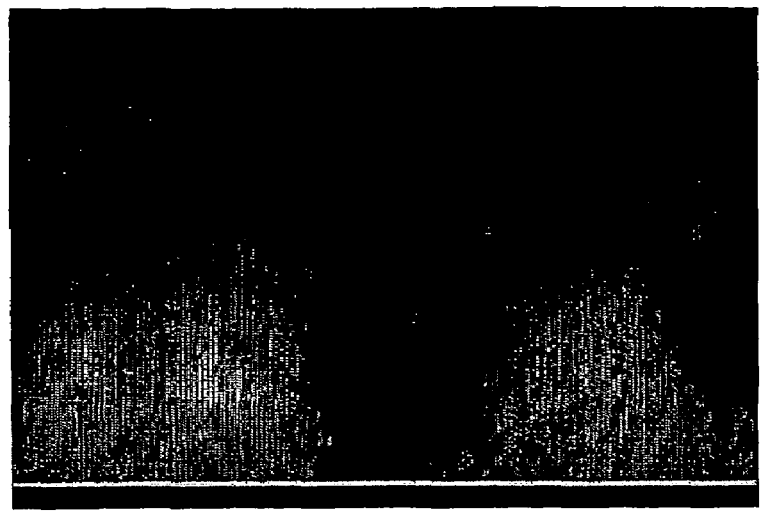
FIGS. 4A-F depict the role of iron in biofilm development.
Figure 4B:
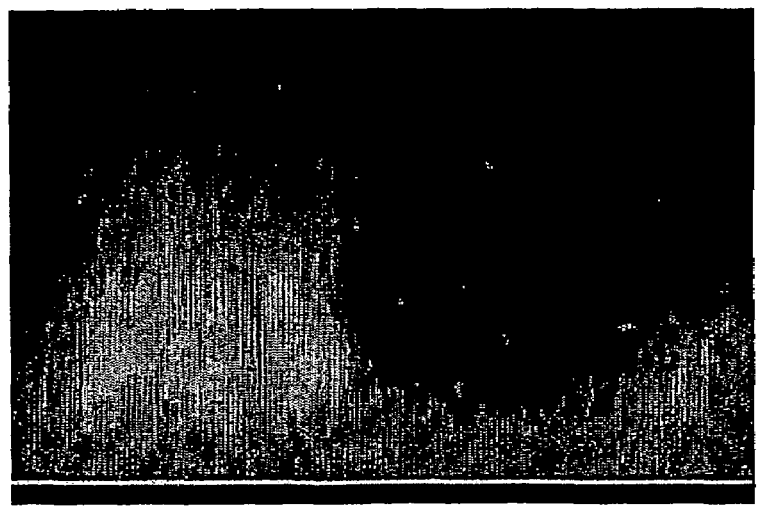
Figure 4C:

The mechanism of lactoferrin's action on biofilm development was investigated. To examine the role of iron, the activity of iron-saturated lactoferrin to iron-unsaturated lactoferrin was compared (FIGS. 4a-c). Unlike iron-unsaturated lactoferrin, iron-saturated lactoferrin did not prevent P. aeruginosa biofilm formation. Conalbumin, a lactoferrin-like chicken egg host defense protein functioned similarly, in that it prevented biofilm formation in the iron-unsaturated state, but not when iron-saturated. These results suggest that lactoferrin blocks P. aeruginosa biofilm formation by sequestering free iron.

Figure 4D:
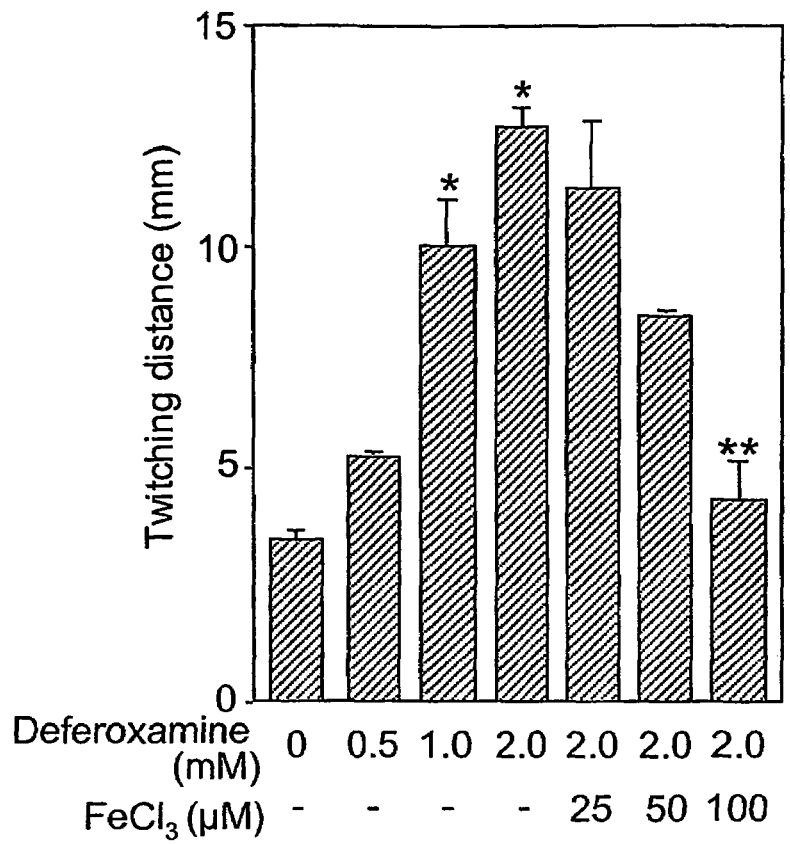

It was hypothesized that the increased surface motility induced by iron chelation was due to twitching, a specialized form of surface locomotion mediated by type 4 pili. To test this, we performed surface motility assays in which P. aeruginosa was inoculated at a point on the bottom of agar plates, and the rate at which bacteria spread over the agar-plastic interface was measured. Because it is more stable than lactoferrin, the iron chelator deferoxamine was used to prepare the agar plates. Deferoxamine stimulated surface motility in a dose-dependent manner and this response was blocked by adding iron (FIG. 4d). Thus, as free iron levels decreased, surface motility increased.

EXAMPLE 4

Biofilm Formation and Stimulation of Surface Motility

Figure 4E:
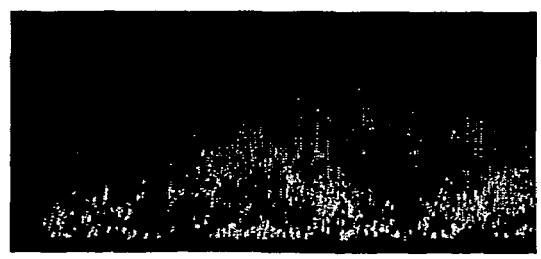
Figure 4F:

To further test whether lactoferrin prevented biofilm development by stimulating surface motility, its effect on a P. aeruginosa surface mutant was examined. It was hypothesized that the mutant would form biofilms in the presence of lactoferrin. FIGS. 4e, f show that the mutant formed microcolonies and irregularly shaped biofilms in both the absence and presence of lactoferrin. This stands in contrast to the surface wild-type strain, where differentiated biofilm formation was completely blocked by lactoferrin (FIGS. 4a, c). Taken together these results indicate that lactoferrin prevents biofilm formation by stimulating bacterial surface motility. Furthermore, the concentration of lactoferrin that had this effect did not limit the growth of free-swimming bacteria and only slightly reduced the growth of attached cells. Once bacteria were living in an established biofilm, they lost sensitivity to lactoferrin.

EXAMPLE 5

Biofilm Formation in the Presence of Lactoferrin and the Effects of Antimicrobials Biofilm bacteria are extraordinarily resistant to killing by antimicrobials. It was hypothesized that the surface attached bacterial layers that formed in the presence of lactoferrin would be less resistant than differentiated biofilms that formed in the absence of lactoferrin. To test this, bacteria were grown in a biofilm reactor on small removable discs. This allowed the antimicrobial susceptibility of the bacterial community to be tested with its multicellular structure intact. Bacteria were grown with or without conalbumin. Conalbumin was used in these studies because the cost of lactoferrin was prohibitive for the large volume of medium required, and as described above, lactoferrin and conalbumin affected biofilm formation similarly. After 48 h, the discs were removed from the reactor (and from the conalbumin), and two agents were tested: $H_2O_2$, which neutrophils utilize in the oxidative killing of bacteria; and tobramycin, an antibiotic used clinically to treat P. aeruginosa infections. Control biofilms were resistant to both agents; 1000 µg/ml tobramycin and 500 mM $H_2O_2$ had minimal effects on viability after 4 h of treatment (FIG. 5). In contrast, growth in conalbumin decreased resistance to both agents in a dose-dependent manner. Thus, in addition to inhibiting structural differentiation, iron chelation limited the development of an important functional consequence of biofilm formation—antimicrobial resistance.

CONCLUSION FROM THE EXAMPLES

For the host, the development of a biofilm infection on a normally sterile mucosal surface can have disastrous consequences. For example, biofilms form in the airways of cystic fibrosis patients and on other compromised mucosal surfaces.

The data from the examples above suggest that lactoferrin has a previously unrecognized role in host defense. In addition to its well-known bactericidal and bacteriostatic actions, it blocks the formation of *P. aeruginosa* biofilms at a low concentration, keeping the bacteria more vulnerable to killing. This function may serve as a fail-safe mechanism to prevent bacteria that survive initial defenses from assuming the intractable biofilm state. Secondary immune responses may then be better able to combat the infecting organisms.

From the bacterial point of view, biofilms are a growth mode specialized for long-term colonization of surfaces. The data indicate that a higher level of iron is required for biofilm formation than is needed for growth. If the iron level is acceptable, *P. aeruginosa* is cued to stop moving, form microcolonies, and eventually develop into biofilms. If iron levels are not sufficient, the *P. aeruginosa* cells keep moving. This response may ensure survival of the bacteria by preventing the construction of complex, durable biofilm structures in locations where iron, a critical nutrient, is in short supply.

Incorporation By Reference

All publications, patent applications, patents, and other references mentioned herein are incorporated by reference. In addition, the materials, methods, and examples are illustrative only and not intended to be limiting.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method of inhibiting biofilm formation by *Pseudomonas aeruginosa* bacteria comprising contacting said bacteria with an effective amount of lactoferrin, wherein bioavailable iron is limited by said lactoferrin, to thereby inhibit biofilm formation by said bacteria.

2. A method of stimulating surface motility in *Pseudomonas aeruginosa* bacteria, comprising contacting said bacteria with an effective amount of lactoferrin, wherein bioavailable iron is limited by said lactoferrin, thereby stimulating surface motility in said bacteria.

3. A method of inhibiting biofilm formation on a piece of equipment by *Pseudomonas aeruginosa* bacteria, comprising contacting said piece of equipment with an effective amount of lactoferrin, wherein bioavailable iron is limited by said lactoferrin, to thereby inhibit biofilm formation on a piece of equipment by said bacteria.

4. A method of inhibiting biofilm formation on a device by *Pseudomonas aeruginosa* bacteria, comprising contacting said device with an effective amount of lactoferrin, wherein bioavailable iron is limited by said lactoferrin, thereby inhibiting the formation of biofilm on said device by said bacteria.

5. A method of inhibiting biofilm formation on food by *Pseudomonas aeruginosa* bacteria, comprising contacting said food with an effective amount of lactoferrin, wherein bioavailable iron is limited by said lactoferrin, thereby inhibiting the formation of biofilm on said food by said bacteria.

6. The method of any one of claims 1, 2, 3, 4, or 5 wherein the concentration of lactoferrin is between 5 and 50 µg/ml.

7. The method of any one of claims 1, 2, 3, 4, or 5 wherein the concentration of lactoferrin is between 15 and 40 µg/ml.

8. The method of any one of claims 1, 2, 3, 4, or 5 wherein the concentration of lactoferrin is between 20 and 30 µg/ml.

9. The method of any one of claims 1, 2, 3, 4, or 5 wherein the concentration of lactoferrin is 20 µg/ml.

10. The method of any one of claims 1, 2, 3, 4, or 5 wherein the concentration of lactoferrin is between 5 and 100 µg/ml.

11. A method of inhibiting biofilm formation by *Pseudomonas aeruginosa* bacteria comprising contacting said bacteria with an effective amount of conalbumin, wherein bioavailable iron is limited by said conalbumin, to thereby inhibit biofilm formation by said bacteria.

12. A method of stimulating surface motility in *Pseudomonas aeruginosa* bacteria, comprising contacting said bacteria with an effective amount of conalbumin, wherein bioavailable iron is limited by said conalbumin, thereby stimulating surface motility in said bacteria.

13. The method of any one of claims 1, 2, 11, or 12, wherein the bacteria are contacted with the lactoferrin or conalbumin prior to a point at which the bacteria stop roaming.

14. A method of inhibiting biofilm formation on a piece of equipment by *Pseudomonas aeruginosa* bacteria, comprising contacting said piece of equipment with an effective amount of conalbumin, wherein bioavailable iron is limited by said conalbumin, to thereby inhibit biofilm formation on a piece of equipment by said bacteria.

15. The method of claim 3 or 14, wherein the equipment is used for a medical, industrial or commercial application.

16. A method of inhibiting biofilm formation on a device by *Pseudomonas aeruginosa* bacteria, comprising contacting said device with an effective amount of conalbumin, wherein bioavailable iron is limited by said conalbumin, thereby inhibiting the formation of biofilm on said device by said bacteria.

17. The method of claim 4 or 16, wherein contacting comprises bathing said device in a solution comprising an effective amount of the lactoferrin or conalbumin.

18. The method of claim 4 or 16, wherein contacting comprises coating said device in a solution comprising an effective amount of the lactoferrin or conalbumin.

19. A method of inhibiting biofilm formation on food by *Pseudomonas aeruginosa* bacteria, comprising contacting said food with an effective amount of conalbumin, wherein bioavailable iron is limited by said conalbumin, thereby inhibiting the formation of biofilm on said food by said bacteria.

20. The method of claim 5 or 19, wherein said food is further contacted with an antibiotic.

21. The method of claim 20, wherein said food is meat.

* * * * *

UNITED STATES PATENT AND TRADEMARK OFFICE
CERTIFICATE OF CORRECTION

PATENT NO. : 7,446,089 B2  Page 1 of 1
APPLICATION NO. : 10/958923
DATED : November 4, 2008
INVENTOR(S) : Pradeep K. Singh et al.

It is certified that error appears in the above-identified patent and that said Letters Patent is hereby corrected as shown below:

At col. 1, line 12, insert the following:

-- GOVERNMENT SUPPORT

This invention was made with U.S. government support under Grant No. HL04173, awarded by the National Institutes of Health. The U.S. government has certain rights in the invention. --

Signed and Sealed this

Fourteenth Day of April, 2009

JOHN DOLL
*Acting Director of the United States Patent and Trademark Office*